United States Patent [19]

Maurer et al.

[11] 4,383,949
[45] May 17, 1983

[54] PREPARATION OF 3-BROMO-4-FLUOROBENZALDEHYDE AND ITS ACETALS

[75] Inventors: Fritz Maurer; Hans-Jochem Riebel, both of Wuppertal; Uwe Priesnitz, Solingen; Erich Klauke, Odenthal, all of Fed. Rep. of Germany

[73] Assignee: Bayer Aktiengesellschaft, Leverkusen, Fed. Rep. of Germany

[21] Appl. No.: 277,585

[22] Filed: Jun. 26, 1981

[30] Foreign Application Priority Data

Jul. 16, 1980 [DE] Fed. Rep. of Germany ....... 3026959

[51] Int. Cl.$^3$ .................. C07C 121/52; C07C 43/313; C07C 47/55; C07C 103/22
[52] U.S. Cl. .............................. 260/465 G; 564/142; 564/183; 568/436; 568/592
[58] Field of Search .............................. 568/592, 436; 260/465 G; 564/142, 183

[56] References Cited

FOREIGN PATENT DOCUMENTS 2732227 2/1979 Fed. Rep. of Germany .
397635 2/1966 Switzerland .
397124 2/1933 United Kingdom .
1166793 10/1969 United Kingdom .

*Primary Examiner*—Dolph H. Torrence
*Attorney, Agent, or Firm*—Sprung, Horn, Kramer & Woods

[57] ABSTRACT

A process for the preparation of a 3-bromo-4-fluorobenzaldehyde acetal of the formula

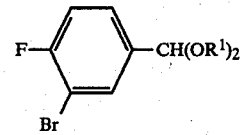

in which
$R^1$ is methyl or ethyl, which comprises reacting a 3-bromo-4-fluoro-benzoic acid halide with ammonia to form 3-bromo-4-fluorobenzoic acid amide, dehydrating said amide to form 3-bromo-4-fluoro-benzonitrile, reacting the nitrile with formic acid in the presence of a catalyst at a temperature between about 0° and 150° C. to form 3-bromo-4-fluorobenzaldehyde, and reacting said aldehyde with $R^1OH$ or a derivative thereof capable of forming an acetal. The amide and nitrile are new compounds. The acetals are known intermediates in the synthesis of pyrethroid-like insecticides.

12 Claims, No Drawings

PREPARATION OF 3-BROMO-4-FLUOROBENZALDEHYDE AND ITS ACETALS

The invention relates to an unobvious process for the preparation of 3-bromo-4-fluoro-benzaldehyde and certain acetals thereof and to new intermediate products for this process and to processes for their preparation.

It is known that 4-fluoro-3-phenoxy-benzaldehyde, which is an intermediate product for pyrethroids having a pesticidal action, is obtained when 4-fluoro-3-phenoxy-benzyl bromide is reacted with hexamethylenetetramine and the product of this reaction is heated with acids (see DO-OS (German Published Specification) No. 2,709,264). However, the yield with this method of synthesis, and also in the case of the preparation of the starting compound from 4-fluoro-3-phenoxy-toluene and N-bromo-succinimide, is not completely satisfactory.

3-Bromo-4-fluoro-benzaldehyde and acetals thereof, and also 4-fluoro-3-phenoxy-benzaldehyde acetals as new intermediate products for the preparation of 4-fluoro-3-phenoxy-benzaldehyde, are also the subject of our pending Application Ser. No. 174,762, filed Aug. 4, 1980, abandoned.

It has also been disclosed that specific aromatic aldehydes are obtained when the corresponding nitriles are reacted with formic acid in the presence of moist Raney nickel (see J. Chem. Soc. (London) 1964 5880-1).

The present patent application now provides a process for the preparation of 3-bromo-4-fluoro-benzaldehyde and 3-bromo-4-fluoro-benzaldehyde acetals of the general formula

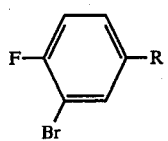

(I)

in which
R represents —CHO or —CH(OR$^1$)$_2$,
in which
R$^1$ represents a methyl or ethyl group,
characterized in that 3-bromo-4-fluoro-benzonitrile of the formula

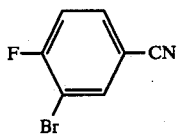

(II)

is reacted with formic acid in the presence of a catalyst at a temperature between about 0° and 150° C. and, if an acetal is required, the aldehyde of the formula

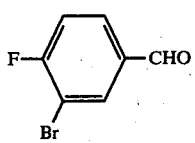

(Ia)

which is thus formed is then acetalized with an agent capable of converting the —CHO radical into a —CH-(OR$^1$)$_2$ radical, in which R$^1$ has the above-mentioned meaning.

The present invention further provides, as a new compound, 3-bromo-4-fluoro-benzonitrile of the formula

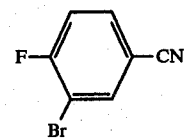

(II)

The present invention further provides a process for the preparation of the 3-bromo-4-fluoro-benzonitrile of the formula (II), characterized in that 3-bromo-4-fluoro-benzoic acid amide of the formula

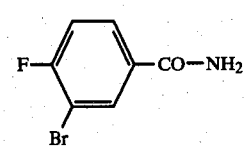

(III)

is dehydrated.

The present invention further provides, as a new compound, 3-bromo-4-fluoro-benzoic acid amide of the formula

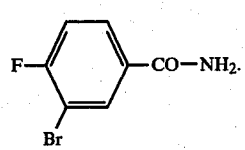

(III)

Finally, the present invention provides a process for the preparation of the 3-bromo-4-fluoro-benzoic acid amide of the formula (III), characterized in that a 3-bromo-4-fluoro-benzoic acid halide of the general formula

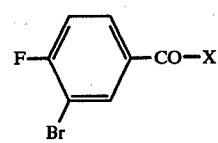

(IV)

in which
X represents a fluorine, chlorine or bromine atom, is reacted with ammonia, optionally in the presence of a diluent.

Surprisingly, 4-fluoro-3-phenoxy-benzaldehyde can be prepared via the above-mentioned new intermediate products in a more simple manner and in a better yield than by the known processes mentioned above.

The new process according to the present invention for the production of a compound of formula (I) is illustrated by the following reaction equation in which Raney nickel is used as the catalyst and orthoformic acid triethyl ester in ethanol is used as the acetalizing agent:

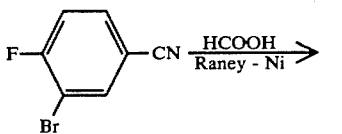

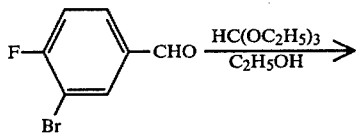

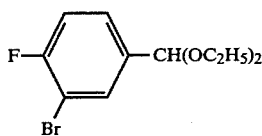

The metal catalysts customarily employed for catalytic hydrogenations can be used as a catalyst for the process according to the present invention for the production of a compound of formula (I). Raney nickel may be mentioned as the preferred catalyst. The catalysts can be employed in the water-moist state.

For the production of a compound of formula (I), the temperature is kept between 0° and 150° C., preferably between 50° and 120° C. The process is carried out under normal pressure or under slightly elevated or reduced pressure.

In the process for the production of a compound of formula (I), formic acid is used as a reactant and as a diluent and accordingly is employed in a large excess, preferably in an amount of between 10 and 50 moles per mole of starting compounds of the formula (II).

In a preferred embodiment of the process according to the invention for the production of a compound of formula (I), the catalyst is suspended in formic acid, the 3-bromo-4-fluoro-benzonitrile of formula (II) is added to this suspension and the reaction mixture is heated for several hours. Working up can be effected by conventional methods, for example by diluting with water, filtering, extracting the filtrate with an organic solvent which is virtually immiscible with water (for example with toluene), drying the extracts, filtering and distilling the filtrate under reduced pressure, 3-bromo-4-fluoro-benzaldehyde being obtained as a colorless liquid.

3-Bromo-4-fluoro-benzaldehyde dimethyl acetal and 3-bromo-4-fluoro-benzaldehyde diethyl acetal have not been described hitherto. They can be prepared not only by the process of the present invention but also by processes which are in principle known. They are obtained, for example, when 3-bromo-4-fluoro-benzaldehyde is reacted with orthoformic acid trimethyl ester or orthoformic acid triethyl ester in the presence of a diluent, (for example toluene and methanol or ethanol,) and optionally in the presence of an ion exchanger as the catalyst, at a temperature between 0° and 100° C., preferably between 10° and 80° C. After this reaction, working up can again be carried out by conventional methods, for example by filtering, washing the filtrate with dilute potassium carbonate solution and distilling under reduced pressure.

The new 3-bromo-4-fluoro-benzonitrile of formula (II), which is to be used as the starting compound in the process according to the invention, for the production of a compound of formula (I), can be prepared from 3-bromo-4-fluoro-benzoic acid amide of formula (II) by dehydration processes which are in themselves known (see Methodicum Chimicum, Volume 6 (1974), pages 654 to 656).

The nitrile of formula (II) is obtained, in a preferred embodiment, when 3-bromo-4-fluoro-benzoic acid amide is added, at about 25° C., to excess thionyl chloride and the mixture is heated at the boil under reflux until the evolution of gas has ceased, and distilled.

The process according to the present invention for the production of the new 3-bromo-4-fluoro-benzoic acid amide of formula (III) by reacting 3-bromo-4-fluoro-benzoic acid halides of the formula (IV) with ammonia is carried out in accordance with methods which are in themselves known (see Methodicum Chimicum, Volume 6 (1974), page 686).

The amide of formula (III) is obtained, in a preferred embodiment, when 3-bromo-4-fluoro-benzoic acid fluoride (and/or the acid chloride and/or the acid bromide of the formula (IV)) is added slowly to an aqueous ammonia solution which has been warmed to a temperature between about 30° and 60° C., and the mixture is stirred for several hours. The product of the formula (III) crystallizes out and can be isolated by filtration.

3-Bromo-4-fluoro-benzoic acid halides of the formula (IV) which are to be used as starting materials, are the subject of our, as yet unpublished, patent application No. corresponding to German Patent application No. P 2 915 738 (Le A 19 590).

For example, a mixture of 3-bromo-4-fluoro-benzoic acid fluoride and 3-bromo-4-fluoro-benzoic acid bromide is obtained when 4-chloro-benzoyl chloride is converted, by reaction with potassium fluoride, into 4-fluorobenzyl fluoride and the latter is then brominated.

4-Chloro-benzoyl chloride is reacted with potassium fluoride, for example in tetramethylene sulphone at temperatures between 200° and 220° C., and the reaction mixture is worked up by distillation. 4-Fluoro-benzoyl fluoride with a boiling point of 53° C./20 mbars (refractive index: $n_D^{20} = 1.4792$) is obtained.

4-Fluoro-benzoyl fluoride is reacted with elementary bromine in the presence of 1% of iron-III chloride at 70° to 75° C. With a batch of 1 mole, on distillation 40 g of unchanged starting materials are recovered and 182 g of a mixture of 3-bromo-4-fluoro-benzoyl fluoride (boiling point: 82°-83° C./15 mbars; refractive index: $n_D^{20} = 1.5315$; melting point: 32°-34° C.) and 3-bromo-4-fluoro-benzoyl bromide (boiling point: 123° C./15 mbars; melting point: 35°-37° C.) are obtained.

3-Bromo-4-fluoro-benzaldehydes, and their acetals, of the formula (I) can be used to prepare 3-phenoxy-4-fluoro-benzaldehyde, which is known as an intermediate product for insecticides (see DO-OS (German Published Specification) No. 2,709,264).

The preparation of 3-phenoxy-4-fluoro-benzaldehyde can, for example, be outlined by the following equation if 3-bromo-4-fluoro-benzaldehyde diethyl acetal and potassium phenolate are used as the starting materials in a first stage and splitting of the acetal, which is to be carried out as a second stage, is effected with an acid, such as hydrochloric acid:

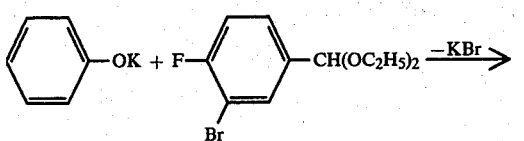

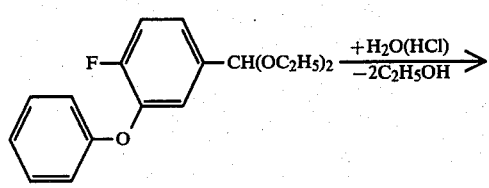

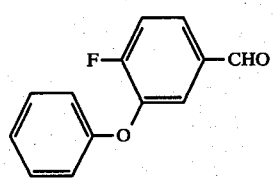

Alkali metal compounds and alkaline earth metal compounds of phenol, which can be used as starting materials in this reaction, are, for example, sodium phenolate, potassium phenolate and magnesium phenolate.

The catalysts used are copper or copper compounds. Examples of such catalysts are copper, copper-I oxide, copper-II oxide, copper-I chloride and copper-I bromide.

The diluents used are preferably aprotic polar solvents. Examples of such solvents are dimethylformamide, dimethylacetamide, N-methypyrrolidone, dimethylsulphoxide, tetramethylene, sulphone, hexamethylphosphoric acid triamide and bis-(2-methoxyethyl)ether (diglyme). The latter is particularly preferred.

The reaction temperature is kept between 100° and 200° C., preferably between 130° and 170° C. The process is usually carried out under normal pressure.

1 to 2 moles, preferably 1.2 to 1.8 moles of phenolate, 0.01 to 0.5 mole, preferably 0.1 to 0.5 mole, of copper catalyst and 100 to 500 ml of diluent are employed per mole of 3-bromo-4-fluoro-benzaldehyde acetal of the formula (I b).

In a preferred embodiment of the reaction, outlined above, for the preparation of 4-fluoro-3-phenoxybenzaldehyde acetals, the phenolate is initially introduced in one of the diluents indicated above, together with the copper catalyst, and the mixture is heated up to the reaction temperature. The 3-bromo-4-fluorobenzaldehyde acetal is then added dropwise and the reaction mixture is stirred for several hours more. Working up can be effected by conventional methods, for example by distilling off the diluent under reduced pressure, dissolving the residue in toluene, filtering, washing the filtrate with dilute sodium hydroxide solution and distilling under reduced pressure. 3-Phenoxy-4-fluoro-benzaldehyde acetals are obtained as colorless liquids in this way.

Saponification of the acetals to 3-phenoxy-4-fluorobenzaldehyde can be carried out by conventional methods. In a preferred procedure, the acetals are mixed with a dilute mineral acid, such as hydrochloric acid or sulphuric acid, and the mixture is stirred for several hours at temperatures between 20° and 60° C. For working up, the mixture is extracted with an organic solvent which is virtually immiscible with water, such as toluene, and the extracts are washed with sodium bicarbonate solution and water and freed from the solvent by distillation under reduced pressure. 3-Phenoxy-4-fluoro-benzaldehyde remains as an oily residue.

In the following preparative examples, Examples 1 to 3 illustrate processes according to the invention for the production of compounds of formula (I), Examples 4 and 5 illustrate processes for the production of compounds of the formula (II) and (III), respectively, according to the invention and Examples 6 and 7 illustrate the use of compounds of formula (I), produced according to the invention, in the production of intermediates for the production of insecticidally active compounds.

PREPARATIVE EXAMPLES

EXAMPLE 1

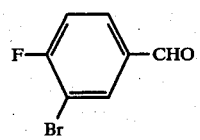

17.0 g of a 50% strength alkaline suspension of Raney nickel were filtered under a nitrogen atmosphere and the material on the filter was washed until neutral. The Raney nickel obtained by this method was suspended in 150 ml of formic acid. 20.0 g (0.1 mole) of 3-bromo-4-fluoro-benzonitrile were added to this suspension. The mixture was heated at 80° to 90° C. for 3 to 5 hours and the reaction mixture was then cooled and poured into 300 ml of water. After filtering, the filtrate was twice extracted with, in each case, 200 ml of toluene. The toluene phase was dried over sodium sulphate and then concentrated. 17.2 g (85% of theory) of 3-bromo-4-fluoro-benzaldehyde with a boiling point of 63°-65° C./0.3 mm Hg were obtained.

EXAMPLE 2

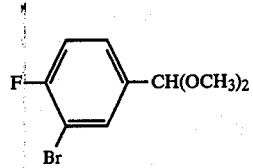

1.5 g of air-dried ion exchanger SPC 118 (H-form of a cation exchanger, strongly acid, macroporous), 16 g (0.5 mole) of methanol and 58.5 g (0.55 mole) of orthoformic acid trimethyl ester were added to a solution of 101.5 g (0.5 mole) of 3-bromo-4-fluorobenzaldehyde in 200 ml of toluene, the mixture was stirred for a further 1 hour without a bath and was then warmed at 50° C. for 2 hours. The reaction mixture was cooled, filtered to remove the ion exchanger and washed with 200 ml of 5% strength potassium carbonate solution. The solvent was then stripped off and the residue was distilled in vacuo. 118 g (95% of theory) of 3-bromo-4-fluorobenzaldehyde dimethyl acetate were obtained in this way, in the form of a colorless liquid with a boiling point of 68° C./0.1 mm Hg.

EXAMPLE 3

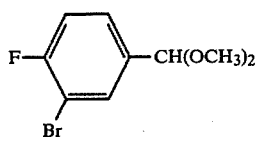

A mixture of 85 g of Raney nickel, which had been washed thoroughly with water, 500 ml of formic acid and 100 g (0.5 mole) of 3-bromo-4-fluoro-benzonitrile was stirred for 24 hours at 90°-100° C. under an atmosphere of a blanketing gas (nitrogen or argon). After cooling to room temperature, 1 liter of water was added and the mixture was extracted twice with 300 ml of toluene. The combined toluene solutions were washed with 200 ml of water, with 200 ml of saturated sodium bicarbonate solution and again with 200 ml of water and then dried by incipient distillation. 1.5 g of air-dried ion exchanger SPC 118, 16 g (0.5 mole) of methanol and 58.5 g (0.55 mole) of orthoformic acid trimethyl ester were then added to the solution, the mixture was stirred for a further 1 hour without a bath and was then warmed at 50° C. for 2 hours. The reaction mixture was cooled, filtered to remove the ion exchanger and washed with 200 ml of 5% strength potassium carbonate solution. The solvent was then stripped off and the residue was distilled in vacuo. 93 g (75% of theory) of 3-bromo-4-fluoro-benzaldehyde dimethyl acetal were obtained in this way, in the form of a colorless liquid with a boiling point of 67°-68° C./0.1 mm Hg.

EXAMPLE 4

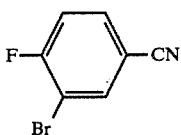

765 g (3.5 moles) of 3-bromo-4-fluoro-benzoic acid amide was added, at 25° C., to 1,150 g (9.7 moles) of thionyl chloride and the mixture was heated under reflux at 85° to 90° C., while stirring, until virtually no further evolution of gas took place. The excess thionyl chloride was then distilled off and the residue was fractionated in a short column. 630 g (91% of theory) of 3-bromo-4-fluoro-benzonitrile with a boiling point of 115°-116° C./20 mm Hg were obtained.

EXAMPLE 5

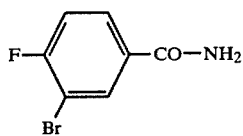

800 g (3.6 moles) of 3-bromo-4-fluoro-benzoyl fluoride were metered into 760 g of 25% strength aqueous ammonia solution (11 moles of NH$_3$), which had been diluted with a further 760 ml of water, at a rate such that an internal temperature of 40° to 50° C. was maintained by the weakly exothermic reaction. After stirring for a further 30 minutes, the crystalline product was isolated by filtration, washed with water and dried. 765 g (97% of theory) of 3-bromo-4-fluoro-benzoic acid amide with a melting point of 131°-133° C. were obtained.

EXAMPLE 6

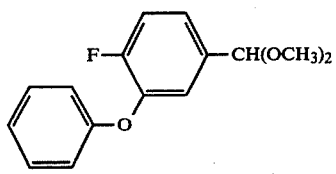

0.4 g of copper-I bromide and 43.5 g (0.375 mole) of sodium phenolate were added to 95 ml of diethylene glycol dimethyl ether (diglyme). The temperature of the mixture rose to about 80° C. To effect dehydration, 15 ml of diglyme (boiling point 160° C.) were distilled off under normal pressure. 57.3 g (0.23 mole) of 3-bromo-4-fluoro-benzaldehyde dimethyl acetal were then added dropwise in the course of 10 minutes, at 150°-155° C., and the reaction mixture was stirred for a further 7 hours at 155° C. Gas chromatography indicated that all of the precursor had then been converted. Subsequently, the solvent was distilled off at 40° C./10 mm Hg, the residue was dissolved in 300 ml of toluene and, after adding 10 g of "Celite" (Trade Mark) 545 as a filter aid, the mixture was filtered to remove the inorganic material. The filtrate was washed with twice 100 ml of 50% strength sodium hydroxide solution, the solvent was then stripped off in vacuo and the residue was distilled in vacuo. 45.5 g (75. of theory) of 3-phenoxy-4-fluoro-benzaldehyde dimethyl acetal were thus obtained in the form of a colorless oil with a boiling point of 128°-130° C./0.1 mm Hg.

EXAMPLE 7

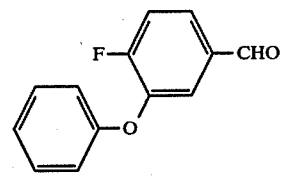

A mixture of 100 ml of 20% strength sulphuric acid and 52.4 g (0.2 mole) of 3-phenoxy-4-fluorobenzaldehyde dimethyl acetal was stirred for 4 hours at 45°-50° C. and then cooled to room temperature. The aldehyde was taken up in 100 ml of toluene and the solution was washed with 100 ml of saturated sodium bicarbonate solution and with 100 ml of water. All of the solution was then distilled off in vacuo, 42 g (97% of theory) of 3-phenoxy-4-fluorobenzaldehyde remained, and according to analysis by gas chromatography, this compound had a purity of 96.6%.

It will be appreciated that the instant specification and examples are set forth by way of illustration and not limitation, and that various modifications and changes may be made without departing from the spirit and scope of the present invention.

We claim:

1. A process for the preparation of a 3-bromo-4-fluorobenzaldehyde acetal of the formula

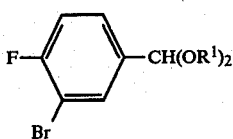

in which

R¹ is methyl or ethyl, which comprises reacting a 3-bromo-4-fluoro-benzoic acid halide with ammonia to form 3-bromo-4-fluoro-benzoic acid amide, dehydrating said amide to form 3-bromo-4-fluoro-benzonitrile, reacting the nitrile with formic acid in the presence of a catalyst at a temperature between about 0° and 150° C. to form 3-bromo-4-fluoro-benzaldehyde, and reacting said aldehyde with R¹OH or a derivative thereof capable of forming an acetal.

2. A process according to claim 1, wherein the catalyst is Raney nickel.

3. A process according to claim 1, wherein the reaction with formic acid is carried out at a temperature between about 50° and 120° C.

4. A process according to claim 1, wherein the formic acid is used in an amount of between 10 and 50 moles per mole of the nitrile.

5. A process according to claim 1, wherein the catalyst is suspended in formic acid, the nitrile is added to this suspension and the reaction mixture is heated for several hours to give the aldehyde.

6. A process according to claim 1, wherein the amide is added, at about 25° C., to excess thionyl chloride and the mixture is heated at the boil under reflux until the evolution of gas has caused to form the nitrile.

7. A process according to claim 1, wherein the 3-bromo-4-fluoro-benzoic acid halide is added slowly to an aqueous ammonia solution which has been warmed to a temperature between about 30° and 60° C., the mixture is stirred for several hours and the amide crystallizes out.

8. A process for the preparation of 3-bromo-4-fluoro-benzaldehyde of the formula

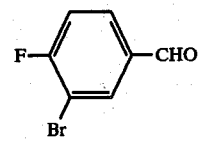

which comprises reacting 3-bromo-4-fluoro-benzonitrile of the formula

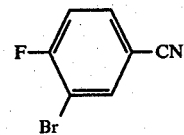

with formic acid in the presence of a catalyst at a temperature between about 0° and 150° C.

9. 3-Bromo-4-fluoro-benzonitrile of the formula

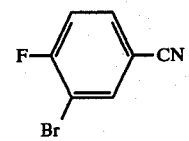

10. A process for the preparation of 3-bromo-4-fluorobenzonitrile according to claim 9, comprising dehydrating 3-bromo-4-fluoro-benzoic acid amide of the formula

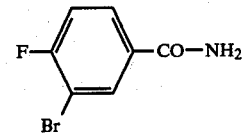

11. 3-Bromo-4-fluoro-benzoic acid amide of the formula

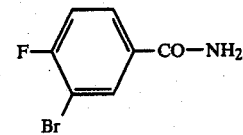

12. A process for the preparation of 3-bromo-4-fluoro-benzoic acid amide according to claim 11, comprising reacting a 3-bromo-4-fluoro-benzoic acid halide with ammonia.

* * * * *

UNITED STATES PATENT AND TRADEMARK OFFICE
CERTIFICATE OF CORRECTION

PATENT NO. : 4,383,949

DATED : May 17, 1983

INVENTOR(S) : Fritz Maurer et al

It is certified that error appears in the above-identified patent and that said Letters Patent is hereby corrected as shown below:

Col. 6, line 6          Delete "in" and insert --In--

Col. 9, line 43       Delete "caused" and insert
(Claim 6)               --ceased--

Signed and Sealed this

Twenty-third Day of August 1983

[SEAL]

Attest:

GERALD J. MOSSINGHOFF

Attesting Officer     Commissioner of Patents and Trademarks